United States Patent [19]

Tatsuoka et al.

[11] Patent Number: 4,774,241
[45] Date of Patent: Sep. 27, 1988

[54] DERIVATIVE OF BENZOQUINONYLPHENYL ALKANOIC ACID AMIDE

[75] Inventors: Toshio Tatsuoka, Nishinomiya; Kenji Suzuki, Osaka; Kayoko Imao, Ikoma; Fumio Satoh, Nagaokakyo; Seiji Miyano, Fukuoka; Kunihiro Sumoto, Oonojo, all of Japan

[73] Assignee: Suntory Limited, Osaka, Japan

[21] Appl. No.: 30,557

[22] Filed: Mar. 27, 1987

[30] Foreign Application Priority Data

Mar. 29, 1986 [JP] Japan ................. 61-069771
Jul. 23, 1986 [JP] Japan ................. 61-171703

[51] Int. Cl.$^4$ ............... A61K 31/495; C07D 295/00; C07D 295/10
[52] U.S. Cl. ................. 514/227.5; 514/255; 514/822; 514/824; 514/879; 514/929; 514/237.5; 544/59; 544/172; 544/386
[58] Field of Search ............ 544/172, 59, 386, 174; 260/396 R; 514/222, 234, 255, 879, 824, 822, 929

[56] References Cited

U.S. PATENT DOCUMENTS 4,478,838 10/1984 Itho et al. .................. 544/386
4,639,452 1/1987 Platel et al. ................. 544/386

FOREIGN PATENT DOCUMENTS 0025692 3/1981 European Pat. Off. ......... 514/234
61-44840 3/1986 Japan ..................... 260/396 R Primary Examiner—Glennon H. Hollrah
Assistant Examiner—Raymond Covington
Attorney, Agent, or Firm—Burns, Doane, Swecker & Mathis

[57] ABSTRACT

A derivative of benzoquinonylphenyl alkanoic acid amide having the formula:

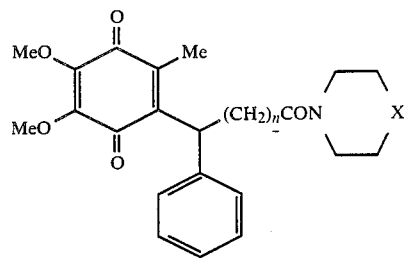

wherein X represents an oxygen atom, sulfur atom, or methylated nitrogen atom, Me represents methyl, and n is 2 or 3. This derivative is effective as a cerebral insufficiency improver.

4 Claims, No Drawings

DERIVATIVE OF BENZOQUINONYLPHENYL ALKANOIC ACID AMIDE

BACKGROUND OF THE INVENTION

1. Field of the Invention

The present invention relates to novel derivatives of benzoquinonylphenyl alkanoic acid amides and pharmaceutically acceptable salts thereof, and a cerebral insufficiency improver containing the same. These compounds can be widely utilized because they are effective for ameliorating and curing (or treating) various symptoms based on "cerebral organic disorders" and "pathergasia".

The term "cerebral organic disorders" used herein means various symptoms derived from cerebral ischemic diseases such as cerebral infarct sequela, cerebral hemorrhage sequela, and cerebral arteriosclerosis sequela and various organic disorders derived from senile dementia, dementia presenilis, amnesia, cephalic traumatic sequela, and cerebral operation sequela. Furthermore, the term "pathergasia" used herein means psychogender organic diseases derived from mania, melancholia, neurosis, Parkinson's disease, schizophrenia, schizophrenia-like disorders, and chorea (Huntington's chorea) as well as medicines and alcoholic beverages.

2. Description of the Related Art

Cerebral cells retain their own intracellular environments which are completely different from the surrounding environments, i.e., extracellular fluids, and while this difference is maintained, the cerebral cells are alive. Accordingly, energy must be always generated and supplied to cerebral cells. Most of the energy required by cerebral nerve cells is supplied by oxygen and glucose. These energy sources are not substantially stored in the brain and, therefore, are always supplied from the blood.

If certain cerebral disturbances or disorders occur, and if the supply of oxygen and glucose to the brain is stopped, generally there is a gradual or stepwise degression in energy metabolism. As a result, the cells lose their functions with the elapse of time, and the cells are soon organically broken. Thus, the cerebral cells cannot effect their normal functions. Therefore, a mechanism to adjust cerebral bloodstreams in the cerebral blood vessels themselves has been fully developed to stably supply the energy sources to the cerebral tissues and to maintain the outer environments of cerebral nerve cells.

Various cerebral circulating improvers, cerebral vasodilators, and cerebral excitometabolites have been heretofore used for the medical treatment of cerebral blood vessel disorders. But, although these medicines are effective for ameliorating subjective symptoms, no substantial amelioration of neutral symptoms and mental symptoms has been observed.

On the other hand, Japanese Unexamined Patent Publication (Kokai) No. 61-44840 discloses various derivatives of benzoquinonyl alkanoic acids, which are described as effective as an antiasthmatic agent, an antiallergic agent or a cerebral circulating improver.

SUMMARY OF THE INVENTION

An object of the present invention is to provide a novel compound having effective activities for ameliorating and curing (or treating) various symptoms caused by the above-mentioned various cerebral disorders or brain syndromes.

Other objects and advantages of the present invention will be apparent from the following description.

In accordance with the present invention, there is provided a derivative of benzoquinonylphenyl alkanoic acid amide having the formula:

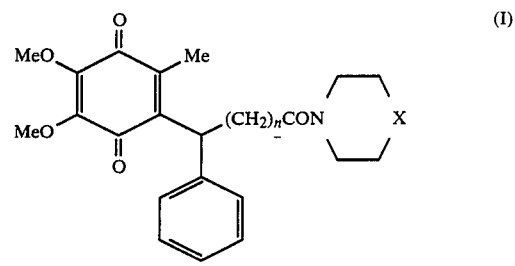

wherein X represents oxygen atom, sulfur atom, or methylated nitrogen atom, Me represents methyl, and n is 2 or 3, or the pharmaceutically acceptable salt thereof.

DESCRIPTION OF THE PREFERRED EMBODIMENTS

The present inventors have found that various derivatives of benzoquinonylphenyl alkanoic acid amides, especially those which are not specifically taught in the above-mentioned Japanese Patent Kokai Publication, have an excellent anticerebral ischemic activity and antihypoxia activity. That is, the derivatives of the benzoquinonylphenyl alkanoic acid amides having the general formula (I) according to the present invention are extremely effective against cerebral anoxia of test animals, at a low dose, and therefore, are an effective improver of or remedy for cerebral organic disorders.

The typical compounds represented by the general formula (I) are as follows:

4-(3,4-Dimethoxy-6-methyl-2,5-benzoquinonyl)-4-phenyl-1-thiomorpholino-1-oxobutane,
4-(3,4-Dimethoxy-6-methyl-2,5-benzoquinonyl)-4-phenyl-1-morpholino-1-oxobutane,
4-(3,4-Dimethoxy-6-methyl-2,5-benzoquinonyl)-4-phenyl-1-(N-methylpiperazinyl)-1-oxobutane,
5-(3,4-Dimethoxy-6-methyl-2,5-benzoquinonyl)-5-phenyl-1-thiomorpholino-1-oxopentane,
5-(3,4-Dimethoxy-6-methyl-2,5-benzoquinonyl)-5-phenyl-1-morpholino-1-oxopentane, and
5-(3,4-Dimethoxy-6-methyl-2,5-benzoquinonyl)-5-phenyl-1-(N-methylpiperazinyl)-1-oxopentane.

The compounds having the general formula (I) can be prepared as follows:

That is, the compounds having the formula (Ia):

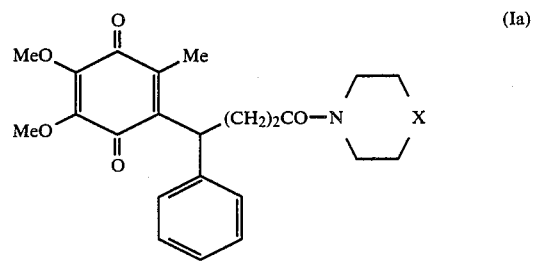

wherein X is as defined above can be prepared by reacting known compounds, γ-phenyl-γ-butyrolactone and 2,3-dimethoxy-5-methyl-1,4-hydroquinone, in the presence of an acid, e.g., polyphosphoric acid, to obtain benzoxepin-2-one derivatives having the general formula (II):

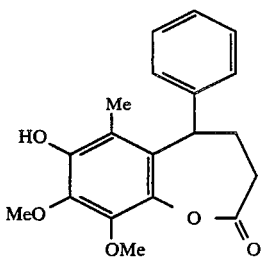

(II)

The compound (II) is reacted with thiomorpholine, morpholine, or N-methylpiperazine to obtain the compounds having the general formula (III):

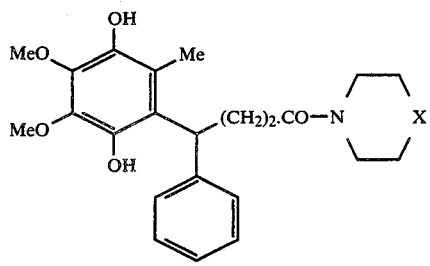

(III)

wherein X is as defined above.

The compounds (III) obtained above can be readily oxidized with an appropriate oxidizing agent such as ferric chloride, silver oxide, or ceric ammonium nitrate obtain the compounds having the above-mentioned general formula (Ia).

On the other hand, the compounds having the general formula (Ib) according to the present invention

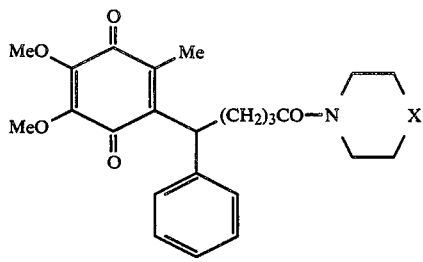

(Ib)

wherein X is defined above, can be prepared by condensation reacting the compound having the formula (IV),

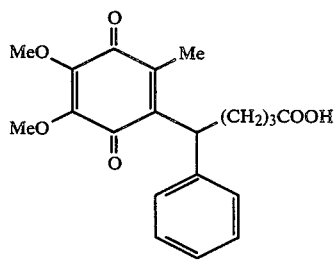

(IV)

which is disclosed in the above-mentioned Japanese Kokai No. 61-44840, with morpholine, thiomorpholine, or N-methylpiperazine in an inert solvent such as methylene chloride, in the presence of 1,3-dicyclohexyl carbodiimide or 1-ethyl-3-(dimethylaminopropyl)carbodiimide hydrochloride (i.e., "DCC").

As mentioned above, the derivatives of benzoquinonylphenyl alkanoic acid amides having the formula (I) according to the present invention are effective for ameliorating and curing various symptoms based on cerebral organic disorders and pathergasia. This is clear from the below-mentioned Evaluation Examples, because the present compounds (I) are effective for test animals having various cerebral anoxia and have an excellent antihypoxia activity against such test animals.

When the present derivatives are used as a medicine, there are no critical limitations to the administration methods.

The compounds having the general formula (I) according to the present invention can be administered alone or in combination with pharmaceutically acceptable conventional carrier's, excipients, and fillers in a variety of dosage forms such as tablets, troches, pills, granules, powders, capsules, ampules, suppositories and the like. The excipients include, for example, starch, dextrin, sucrose, lactose, silic acid, carboxymethylcellulose, cellulose, geratin, polyvinylpyrrolidone, glycerin, agar, calcium carbonate, sodium bicarbonate, paraffin, cetyl alcohol, stearic acid esters, kaolin, bentonite, talc, calcium stearate, magnesium stearate, polyethyleneglycol, water, ethanol, isopropyl alcohol, propyleneglycol and the like. The present compounds also may be, for example, parenterally administered, in the form of, for example, injections or suppositories.

Although there are no critical limitations to the dose range of the present cerebral insufficiency improver, the optimum dose range of the compound (I) of the present invention is 0.1–1000 mg, preferably 10 to 500 mg, per day. This dose range can be suitably changed depending upon, for example, the characteristics of the subjects including age, response, weight, severity of disease and the like, the administration methods, the dosage forms, and the dosing frequency.

EXAMPLES

The present invention now will be further illustrated by, but is by no means limited to, the following Synthesis Examples, Formulation Examples, and Evaluation Examples.

REFERENCE EXAMPLE

Preparation of
8,9-Dimethoxy-7-hydroxy-6-methyl-5-phenyl-2-oxo-2,3,4,5-tetrahydro-1-benzoxepin

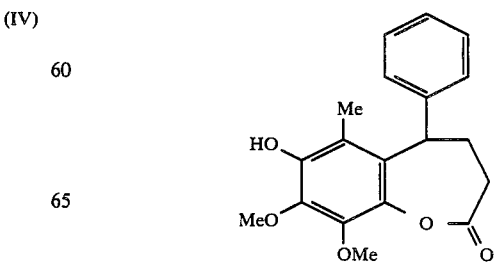

A 752 mg amount of 2,3-Dimethoxy-5-methyl-1,4-hydroquinone and 795 mg of γ-phenyl-γ-butyrolactone were added to 80 ml of polyphosphoric acid and the mixture was stirred at room temperature for 5 hours. The reaction mixture was poured into ice water, followed by extracting with ethyl ether. The extracted solution was washed with water and dried over anhydrous magnesium sulfate, and the solvent was then distilled off. The residue was subjected to a silica gel column by using hexane/ethyl acetate (3:1) as a solvent. Thus, 249 mg of the desired purified compound was obtained (yield=18.6%).

The physical properties of the resultant compound are as follows:
State: oily substance
IR spectrum (CHCl$_3$, $\nu_{max}$cm$^{-1}$): 3500, 1752
NMR spectrum (δ ppm): 2.21(3H, s), 2.30–2.70 (3H, m), 2.80–3.00 (1H, m), 3.83 (3H, s), 3.99 (3H, s), 4.55–4.70 (1H, m), 5.86 (1H, s), 7.10–7.35 (5H, m)

SYNTHETIC EXAMPLE 1

Preparation of 4-(3,4-dimethoxy-6-methyl-2,5-benzoquinonyl)-4-phenyl-1-thiomorpholine-1-oxobutane A 380 mg amount of the benzoxepin-2-one derivative prepared in Reference Example and 597 mg of thiomorpholine were heated under reflux for 5 hours in toluene. The reaction mixture was concentrated under a reduced pressure and the residue was dissolved in 85% aqueous methanol. To the resultant solution, 22 g of ferric chloride was added, followed by stirring at room temperature for 15 minutes, and the reaction mixture was then poured into water. The mixture was extracted with ethyl acetate, and the extract was washed with water and dried over anhydrous magnesium sulfate. The solvent was distilled off and the residue was purified by silica gel column chromatography using a hexane-ethyl acetate (1:1) solvent. Thus, 231 mg (yield=46.5%) of the desired compound was obtained.

The physical properties of the desired compound are shown in Table 1.

SYNTHETIC EXAMPLE 2

Preparation of 4-(3,4-dimethoxy-6-methyl-2,5-benzoquinonyl)-4-phenyl-1-morpholino-1-oxobutane A 280 mg amount of the benzoxepin-2-one derivative prepared in Reference Example and 111 mg of morpholine were heated under reflux for 10 hours. The reaction mixture was concentrated under a reduced pressure and the residue was dissolved in 75% aqueous methanol. To the resultant solution, 1.40 g of ceric ammonium nitrate was added, followed by stirring at room temperature for 20 minutes. The reaction product was purified in the same manner as in Synthetic Example 1, and thus 240 mg (yield=68.1%) of the desired compound was obtained.

The physical properties of the resultant compound are shown in Table 1.

SYNTHETIC EXAMPLE 3

Preparation of 4-(3,4-Dimethoxy-6-methyl-2,5-benzoquinonyl)-4-phenyl-1-(N-methylpiperazinyl)-1-oxobutane A 678 mg amount of the benzoxepin-2-one derivative and 310 mg of N-Methylpiperazine were reacted and treated in the same manner as in Synthetic Example 1. Thus, 510 mg (yield=57.9%) of the desired compound was obtained.

The physical properties of the resultant compound are shown in Table 1.

SYNTHETIC EXAMPLE 4

Preparation of 5-(3,4-dimethoxy-6-methyl-2,5-benzoquinonyl)-5-phenyl-1-thiomorpholino-1-oxopentane A 530 mg amount of 5-(3,4-dimethoxy-6-methyl-2,5-benzoquinonyl)-5-phenylpentanoic acid and 229 mg of thiomorpholine were dissolved in 60 ml of methylene chloride. To the resultant solution, 426 mg of DCC was added, followed by stirring at room temperature for 2 hours. The reaction mixture was poured into water, followed by extracting with methylene chloride, and the extracted solution was purified in the same manner as in synthetic Example 1. Thus, 398 mg (yield=60.7%) of the desired compound was obtained.

The physical properties of the resultant compound are shown in Table 1.

SYNTHETIC EXAMPLE 5

Preparation of 5-(3,4-dimethoxy-6-methyl-2,5-benzoquinonyl)-5-phenyl-1-morpholino-1-oxopentane The desired compound was prepared in the same manner as in Synthetic Example 4, except that morpholine was used instead of the thiomorpholine. The yield was 61.3%.

The physical properties of the resultant compound are shown in Table 1.

SYNTHETIC EXAMPLE 6

Preparation of 5-(3,4-dimethoxy-6-methyl-2,5-benzoquinonyl)-5-phenyl-1-(N-methylpiperazinyl)-1-oxopentane The desired compound was prepared in the same manner as in Synthetic Example 4, except that N-methylpipererazine was used instead of the thiomorpholine. The yield was 74.9%.

The physical properties of the resultant compound are shown in Table 1.

TABLE 1

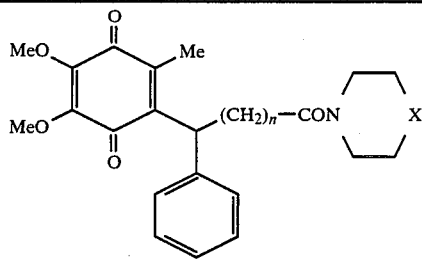

| Example No. | n | X | Yield (%) | m.p. (°C.) | IR spectrum (CHCl$_3$, $\nu_{max}$ cm$^{-1}$) | NMR spectrum (δ ppm) | | MS spectrum Elementary analysis |
|---|---|---|---|---|---|---|---|---|
| 1 | 2 | S | 46.5 | m.p. 128–129 | 1640 | 2.60 (3H, s), 2.20–2.70 (8H, m), 3.55–3.70 (2H, m), 3.75–3.95 (2H, m) 3.97 (3H, s), 3.98 (3H, s), 4.38 (1H, t) 7.15–7.35 (5H, m) | C$_{23}$H$_{27}$O$_5$NS Mass: Anal. Calcd. Found. | 429 (M$^+$) 311 (100) C: 64.31 H: 6.34 N: 3.26 C: 64.17 H: 6.45 N: 3.21 |
| 2 | 2 | O | 68.1 | m.p. 74–76 | 1640 | 2.05 (3H, s), 2.15–2.75 (4H, m) 3.25–3.45 (2H, m), 3.45–3.75 (6H, m) 3.97 (6H, s), 4.38 (1H, t), 7.10–7.40 (5H, m) | C$_{23}$H$_{27}$O$_6$N Mass: Anal. Calcd. Found. | 413 (M$^+$) 284 (100) C: 66.81 H: 6.58 N: 3.39 C: 66.74 H: 6.82 N: 3.34 |
| 3 | 2 | H—CH$_3$ | 57.9 (31.3) | m.p. 97–99 (HCl salt) | 1638 (free amine) | 2.09 (3H, s), 2.30 (3H, s), 2.20–2.75 (8H, m), 3.30–3.45 (2H, m), 3.55–3.70 (2H, m), 3.88 (6H, s) 4.40 (1H, t) 7.10–7.40 (5H, m) | C$_{24}$H$_{30}$O$_5$N$_2$ Mass: | (HCl) 426 (M$^+$) 98 (100) |
| 4 | 3 | S | 60.7 | m.p. 136–138 | 1641 | 1.45–1.75 (2H, m) 2.05 (3H, S) 2.05–2.35 (2H, m) 2.35 (2H, t) 2.45–2.70 (4H, m) 3.55–4.00 (4H, m) 3.97 (6H, S) 4.31 (1H, t) 7.05–7.45 (5H, m) | C$_{24}$H$_{29}$O$_5$NS Mass: | 443 (M$^+$) |
| 5 | 3 | O | 61.3 | m.p. 106–108 | 1642 | 1.40–1.80 (2H, m) 2.05 (3H, S) 2.05–2.35 (2H, m) 2.34 (2H, t) 3.30–3.75 (8H, m) 3.97 (6H, S) 4.31 (1H, t) 7.05–7.45 (5H, m) | C$_{24}$H$_{29}$O$_6$N Mass: | 427 (M$^+$) |
| 6 | 3 | N—CH$_3$ | 74.9 (50.8) | Oil Hygroscopic Powder (HCl) | 1640 | 1.45–1.85 (2H, m) 2.06 (3H, S) 2.05–2.60 (8H, m) 2.30 (3H, S) 3.30–3.70 (4H, m) 3.97 (6H, S) 4.30 (1H, t) 7.05–7.45 (5H, m) | C$_{25}$H$_{32}$O$_5$N$_2$ Mass: | (HCl) 440 (M$^+$) |

FORMULATION EXAMPLE 1
PREPARATION OF CAPSULE

| Ingredient | mg |
|---|---|
| (1) Compound of Synthetic Example 1 | 50 |
| (2) Lactose | 59.5 |
| (3) Corn starch | 40 |
| (4) Light silicic anhydride | 0.5 |
| Total | 150 mg |

The above-mentioned ingredients were thoroughly mixed in a conventional manner, and the resultant mixture filled into gelatin capsules.

FORMULATION EXAMPLE 2
PREPARATION OF TABLET

| Ingredient | mg |
|---|---|
| (1) Compound of Synthetic Example 1 | 50 |
| (2) Lactose | 48 |
| (3) Corn starch | 50 |
| (4) Poly vinyl pyrolidone | 1.5 |
| (4) Magnesium stearate | 0.5 |
| Total | 150 mg |

The above-mentioned ingredients were mixed and tableted in a conventional manner, to obtain, the desired tablets.

EVALUATION EXAMPLE

The present compounds have low toxicities and excellent cerebral protecting activities (e.g., an excellent anti-cerebral ischemic activity and antihypoxia activity) as shown below.

The activities of some compounds prepared in the above-mentioned Synthetic Examples and the Comparative Examples were evaluated as follows. The results are shown in Table 2.

1. Hypobaric Hypoxia Activity

Male ddY mice having a body weight of 22 to 30 g were used (i.e., 7 to 10 mice in one group). The mice were placed in a desiccator having a volume of about 1 liter and the desiccator was evacuated and then, the sample compound was intraperitoneally injected adjusted by a vacuum pump to a pressure of 180 mmHg. into the mice. The desiccator was evacuated 30 minutes after the injection and the time from the start of the evacuation to the termination of breathing by the mice was determined to be the survival time. If a mouse was still alive 15 minutes after exposure to the hypoxia, the survival time was assumed to be 15 minutes. The results were compared with a control group, to which only a liquid medium (e.g., physiological saline) was injected.

2. Global Ischemia Activity

Male ddY mice having a body weight of 22 to 30 g were used (i.e., 6 mice in one group). The sample compound was intraperitoneally injected into the mice and the mice were decapitated 30 minutes after the injection. After decapitation, the gasping times were determined. The results were compared with a control group to which only the liquid medium (i.e., physiological saline) was injected.

3. Aute Toxicity Test

Male ddY-STF mice having an age of 4 to 5 weeks and a body weight of 22 to 30 g were used for evaluating the acute toxicity of the present compounds. The sample compound was suspended in 1% arabic gum and was intraperitoneally injected. The compounds according to the present invention all had a low toxicity and no substantial toxic symptom was observed even at a dose of 1000 mg/kg,ip.

TABLE 2

| Example No. (Compound) | Hypobaric Hypoxia (Minimum effective dose; mg/kg, ip) | Global Ischemia (Minimum effective dose; mg/kg, ip) | $LD_{50}$ (mg/kg, ip) |
|---|---|---|---|
| 1 | 6.25 | 12.5 | >1,000 |
| 3 | 25 | no effect at 25 mg/kg | — |
| 4 | 6.25 | no effect at 25 mg/kg | >1,000 |
| 5 | 6.25 | no effect at 25 mg/kg | >1,000 |
| Comparative Compound-1[*1] | no effect at 25 mg/kg | no effect at 25 mg/kg | >500 |
| Comparative Compound-2[*2] | no effect at 50 mg/kg | no effect at 25 mg/kg | >500 |
| Comparative Compound-3[*3] | no effect at 50 mg/kg | negative effect at 25 mg/kg[*4] | >500 |

[*1] 4-(3,4-Dimethoxy-6-methyl-2,5-benzoquinonyl)-4-phenylbutyric acid
[*2] 5-(3,4-Dimethoxy-6-methyl-2,5-benzoquinonyl)-5-phenylvaleric acid
[*3] 7-(3,4-Dimethoxy-6-methyl-2,5-benzoquinonyl)-7-phenylheptanoic acid
[*4] Gasping time was shortened.

As is clear from the results shown in Table 2, the present compounds exhibited effective activities in the hypobaric hypoxia test when compared to the comparative carboxylic acid derivatives. Thus, the present compounds are effective as a cerebral insufficiency improver.

We claim:

1. A derivative of benzoquinonylphenyl alkanoic acid amide having the formula:

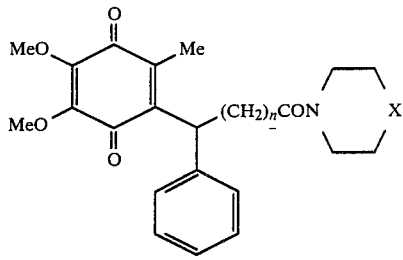

wherein X represents an oxygen atom, sulfur atom, or methylated nitrogen atom, Me represents methyl, and n is 2 or 3 or the pharmaceutically acceptable salt thereof.

2. A compound of claim 1, which is at least one compound selected from the group consisting of
4-(3,4-dimethoxy-6-methyl-2,5-benzoquinonyl)-4-phenyl-1-thiomorpholino-1-oxobutane,
4-(3,4-dimethoxy-6-methyl-2,5-benzoquinonyl)-4-phenyl-1-morpholino-1-oxobutane,
4-(3,4-dimethoxy-6-methyl-2,5-benzoquinonyl)-4-phenyl-1-(N-methylpiperazinyl)-1-oxobutane,
5-(3,4-dimethoxy-6-methyl-2,5-benzoquinonyl)-5-phenyl-1-thiomorpholino-1-oxopentane,
5-(3,4-dimethoxy-6-methyl-2,5-benzoquinonyl)-5-phenyl-1-morpholino-1-oxopentane, and
5-(3,4-dimethoxy-6-methyl-2,5-benzoquinonyl)-5-phenyl-1-(N-methylpiperazinyl)-1-oxopentane.

3. A cerebral insufficiency improver comprising, as an essential component, a derivative of benzoquinonylphenyl alkanoic acid amide having the formula:

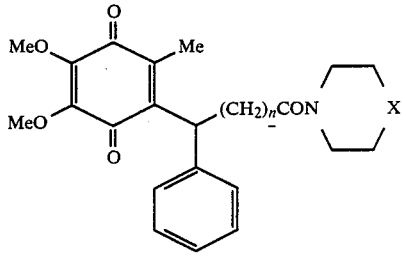

wherein X represents an oxygen atom, sulfur atom, or methylated nitrogen atom, Me represents methyl, and n is 2 or 3, or the pharmaceutically acceptable salt thereof.

4. A cerebral insufficiency improver as claimed in claim 3, wherein said compound is at least one compoudn selected from the group consisting of
4-(3,4-dimethoxy-6-methyl-2,5-benzoquinonyl)-4-phenyl-1-thiomorpholino-1-oxobutane,
4-(3,4-dimethoxy-6-methyl-2,5-benzoquinonyl)-4-phenyl-1-morpholino-1-oxobutane,
4-(3,4-dimethoxy-6-methyl-2,5-benzoquinonyl)-4-phenyl-1-(N-methylpiperazinyl)-1-oxobutane,
5-(3,4-dimethoxy-6-methyl-2,5-benzoquinonyl)-5-phenyl-1-thiomorpholino-1-oxopentane,
5-(3,4-dimethoxy-6-methyl-2,5-benzoquinonyl)-5-phenyl-1-morpholino-1-oxopentane, and
5-(3,4-dimethoxy-6-methyl-2,5-benzoquinonyl)-5-phenyl-1-(N-methylpiperazinyl)-1-oxopentane.

* * * * *